United States Patent
Madsen et al.

(10) Patent No.: US 7,263,997 B2
(45) Date of Patent: **\*Sep. 4, 2007**

(54) RESPIRATORY APPARATUS HAVING AN INSTRUMENT INTRODUCTION SECTION AND MANIFOLD

(75) Inventors: Edward B. Madsen, Riverton, UT (US); William W. Letson, Alpharetta, GA (US)

(73) Assignee: Kimberly-Clark Worldwide, Inc, Neenah, WI (US)

( * ) Notice: Subject to any disclaimer, the term of this patent is extended or adjusted under 35 U.S.C. 154(b) by 426 days.

This patent is subject to a terminal disclaimer.

(21) Appl. No.: 10/430,813

(22) Filed: May 6, 2003

(65) Prior Publication Data

US 2004/0221842 A1 Nov. 11, 2004

(51) Int. Cl.
*A61M 16/00* (2006.01)
*A62B 9/06* (2006.01)

(52) U.S. Cl. ............... 128/207.14; 128/207.16; 128/200.26; 128/912

(58) Field of Classification Search ........... 128/207.14, 128/207.16, 200.26, 912
See application file for complete search history.

(56) References Cited

U.S. PATENT DOCUMENTS

| | | |
|---|---|---|
| 3,991,762 A | 11/1976 | Radford |
| 4,152,017 A | 5/1979 | Abramson |
| 4,416,273 A | 11/1983 | Grimes |
| 4,510,933 A | 4/1985 | Wendt et al. |
| 4,569,344 A | 2/1986 | Palmer |
| 4,573,965 A | 3/1986 | Russo |
| 4,607,635 A | 8/1986 | Heyden |
| 4,638,539 A | 1/1987 | Palmer |
| 4,696,296 A | 9/1987 | Palmer |

(Continued)

FOREIGN PATENT DOCUMENTS

EP 1210957 A1 6/2002

(Continued)

OTHER PUBLICATIONS

U.S. Patent Application BAL-118 (18266), Edward B. Madsen, Filed May 6, 2003.

(Continued)

*Primary Examiner*—Patricia Bianco
*Assistant Examiner*—Nihir Patel
(74) *Attorney, Agent, or Firm*—Dority & Manning, P.A.

(57) ABSTRACT

A respiratory apparatus includes an instrument introduction section that is used for introducing an instrument into an artificial airway of a patient. The instrument introduction section has a distal end and proximal end with an opening which allows for insertion of the instrument into the instrument introduction section. The instrument is movable through the passageway in the instrument introduction section between the proximal and distal ends. A valve is located in the instrument introduction section and has a closed position in which the instrument may be isolated from the artificial airway of the patient. The valve at least substantially blocks the passageway of the instrument introduction section when in the closed position. The valve also has an open position that allows for the instrument to be advanced through the instrument introduction section. A manifold is attached to the distal end of the instrument introduction section. The manifold is in communication with the artificial airway of the patient.

25 Claims, 10 Drawing Sheets

U.S. PATENT DOCUMENTS

| | | | |
|---|---|---|---|
| 4,762,125 A | 8/1988 | Leiman et al. | |
| 4,836,199 A | 6/1989 | Palmer | |
| 4,846,167 A | 7/1989 | Tibbals | |
| 4,872,579 A | 10/1989 | Palmer | |
| D312,880 S * | 12/1990 | Bodai et al. | D24/129 |
| 5,062,420 A | 11/1991 | Levine | |
| 5,083,561 A | 1/1992 | Russo | |
| 5,139,018 A | 8/1992 | Brodsky et al. | |
| 5,199,427 A | 4/1993 | Strickland | |
| 5,218,957 A | 6/1993 | Strickland | |
| 5,220,916 A * | 6/1993 | Russo | 128/207.16 |
| 5,230,332 A | 7/1993 | Strickland | |
| 5,254,098 A | 10/1993 | Ulrich et al. | |
| 5,255,676 A | 10/1993 | Russo | |
| 5,333,606 A * | 8/1994 | Schneider et al. | 128/200.24 |
| 5,349,950 A | 9/1994 | Ulrich et al. | |
| 5,355,876 A | 10/1994 | Brodsky et al. | |
| 5,433,195 A | 7/1995 | Kee et al. | |
| 5,445,141 A | 8/1995 | Kee et al. | |
| 5,513,628 A | 5/1996 | Coles et al. | |
| 5,582,161 A | 12/1996 | Kee | |
| 5,582,165 A | 12/1996 | Bryan et al. | |
| 5,598,840 A | 2/1997 | Iund et al. | |
| 5,628,306 A * | 5/1997 | Kee | 128/203.12 |
| 5,645,048 A | 7/1997 | Brodsky et al. | |
| 5,664,564 A | 9/1997 | Palmer | |
| 5,664,594 A | 9/1997 | Kee | |
| 5,676,136 A | 10/1997 | Russo | |
| 5,694,922 A | 12/1997 | Palmer | |
| 5,711,294 A | 1/1998 | Kee et al. | |
| 5,730,123 A | 3/1998 | Lorenzen et al. | |
| 5,735,271 A * | 4/1998 | Lorenzen et al. | 128/207.16 |
| 5,738,091 A | 4/1998 | Kee et al. | |
| 5,775,325 A | 7/1998 | Russo | |
| 5,779,687 A | 7/1998 | Bell et al. | |
| 5,791,337 A * | 8/1998 | Coles et al. | 128/200.26 |
| 5,882,348 A * | 3/1999 | Winterton et al. | 604/537 |
| 5,919,174 A * | 7/1999 | Hanson | 604/533 |
| 6,012,451 A | 1/2000 | Palmer | |
| 6,026,810 A | 2/2000 | Baird | |
| 6,082,361 A | 7/2000 | Morejon | |
| 6,165,168 A | 12/2000 | Russo | |
| 6,227,200 B1 * | 5/2001 | Crump et al. | 128/207.16 |
| 6,318,368 B1 | 11/2001 | Morejon | |
| 6,494,203 B1 | 12/2002 | Palmer | |
| 6,543,451 B1 * | 4/2003 | Crump et al. | 128/207.14 |
| 6,584,970 B1 * | 7/2003 | Crump et al. | 128/200.24 |
| 6,588,425 B2 * | 7/2003 | Rouns et al. | 128/207.14 |
| 6,602,219 B2 * | 8/2003 | Madsen et al. | 604/27 |
| 6,612,304 B1 * | 9/2003 | Cise et al. | 128/200.26 |
| 6,615,835 B1 * | 9/2003 | Cise et al. | 128/207.14 |
| 6,805,125 B1 * | 10/2004 | Crump et al. | 128/207.16 |
| 6,978,783 B2 * | 12/2005 | Svendsen | 128/207.14 |
| 7,021,313 B1 * | 4/2006 | Crump et al. | 128/207.14 |
| 7,152,603 B1 * | 12/2006 | Crump et al. | 128/207.14 |
| 2002/0078960 A1 | 6/2002 | Cise | |

FOREIGN PATENT DOCUMENTS

| | | |
|---|---|---|
| GB | 2199630 A | 7/1988 |
| WO | WO9531250 | 11/1995 |
| WO | WO9609082 | 3/1996 |
| WO | WO9626757 | 9/1996 |
| WO | WO 0015284 | 3/2000 |
| WO | WO 0024439 | 5/2000 |
| WO | WO 0141853 A1 | 6/2001 |
| WO | WO 0141855 A1 | 6/2001 |
| WO | WO 0145779 A1 | 6/2001 |
| WO | WO 0228463 A2 | 4/2002 |
| WO | WO 0249680 A2 | 6/2002 |
| WO | WO 0249699 A2 | 6/2002 |
| WO | WO 02055143 A2 | 7/2002 |

OTHER PUBLICATIONS

U.S. Patent Application BAL-119 (18267), Edward B. Madsen, Filed May 6, 2003.
PCT Search Report for PCT/US2004/001409, Jun. 18, 2004.
Written Opinion, Jun. 18, 2004.

* cited by examiner

RESPIRATORY APPARATUS HAVING AN INSTRUMENT INTRODUCTION SECTION AND MANIFOLD

BACKGROUND

A variety of different circumstances exist in which a person may be required to have an artificial airway, such as an endotracheal tube, placed in his or her respiratory system. During surgery, for instance, the artificial airway's primary function is to keep the patient's airway open so that adequate lung ventilation can be maintained during the surgical procedure. Alternatively, with many patients the endotracheal tube will remain in place to sustain mechanical ventilation for a prolonged period.

If an endotracheal tube is to be left in place for any substantial amount of time, it is critical that respiratory secretions be periodically removed. This is usually accomplished with the use of a respiratory suction catheter. As the suction catheter is withdrawn, a negative pressure may be applied to the interior of the catheter to draw mucus and other secretions from the respiratory system.

With conventional closed suction catheter assemblies, for example as the one set forth in U.S. Pat. No. 4,569,344 issued to Palmer, which is incorporated herein in its entirety for all purposes, the catheter tube is enveloped by a protective sleeve. The catheter assembly includes a valve mechanism in communication with a vacuum source to control the suctioning process. At its distal or patient end, the closed suction catheter assembly is permanently attached to a manifold, connector, adaptor, or the like.

After the application of negative pressure, the catheter tube may be withdrawn from the artificial airway and, as the catheter tube is pulled back into the protective sleeve, a wiper or seal strips or scrapes a substantial portion of any mucus or secretions from the outside of the catheter tube. However, the distal tip portion of the catheter tube may not pass through the seal or wiper and thus any secretions or mucus on the distal end must be removed by other means. It is desirable to remove these secretions from the catheter tube in order to prevent contamination from infectious agents that may be present in the respiratory secretions. Patients using artificial airways often have compromised immune systems and are more susceptible to infectious agents.

Several mechanisms exist by which a catheter may be cleaned. For example, a lavage port may be included which enables the clinician to inject liquid into the area surrounding the tip of the catheter after it has been withdrawn from the patient's airway. When liquid is injected and suction is applied, the liquid helps to loosen and remove the secretions from the exterior of the catheter.

One significant problem with simply injecting liquid and applying suction is that the suction also causes a volume of respiratory air to be removed through the catheter. The air that is evacuated potentially disrupts the carefully controlled ventilation cycle and the amount of respiratory air available to the patient may be decreased as a result of catheter cleaning.

Prior respiratory suction catheter apparatuses have been developed in order to allow for cleaning of the distal tip of the catheter without substantially interrupting the airflow to the patient from the ventilator. U.S. Pat. No. 6,227,200 B1 issued to Crump et al., which is incorporated herein in its entirety for all purposes, provides in one exemplary embodiment a flap valve that may be used to substantially isolate the distal end of the catheter from the patient's airway during cleaning. The flap valve also has an open position in which the catheter may be inserted through the manifold into the airway of the patient. Current respiratory suction catheter apparatuses incorporate the flap valve and related structure into the manifold such that these parts are permanently bonded to the manifold.

Although respiratory suction catheter apparatuses are provided with a cleaning mechanism in order to remove mucus and other infectious agents, it is often the case that the catheter itself needs to be regularly replaced in order to insure a more sterile respiratory circuit. Some respiratory suction catheter manufacturers recommend replacement of the suction catheter every 24 hours with a new suction catheter. In the instance when the suction catheter needs to be replaced, the manifold into which the flap valve and related parts are contained, and onto which the suction catheter is attached, is detached from the respiratory circuit. This detachment necessarily interferes with the supply of air to the patient, and increases the chances of ventilator associated complications. The new manifold with attached catheter and valve is then connected to the ventilator circuit.

Also, it is often the case that the suction catheter is permanently attached to the structure that houses the valve and related cleaning elements. As such, other instruments which may be desired to be advanced into the artificial airway, such as an endoscope or a bronchoscope, can not be advanced through the manifold. Additionally, these other instruments are not capable of being cleaned by the use of the valve and/or cleaning structure due to the presence of the suction catheter and its attachment to the manifold.

Therefore, there is a need in the art for a respiratory apparatus that is capable of effectively cleaning the tip of an instrument without a resulting drop of ventilation air to the patient. Additionally, a need in the art exists in replacing an instrument with a new instrument without disconnecting the manifold from the ventilation circuit in order to prevent air loss to the patient, and to lower the chances of imparting illness to the patient during the replacement procedure.

SUMMARY

Various features and advantages of the invention will be set forth in part in the following description, or may be apparent from the description, or may be learned from practice of the invention.

The present invention provides for a respiratory apparatus that has an instrument introduction section used for introducing an instrument into an artificial airway of a patient. Different instruments may be releasably attached and inserted through the respiratory apparatus and into the patient's artificial airway.

One exemplary embodiment of the respiratory apparatus includes a manifold that may be configured for connection in communication with an artificial airway of a patient. The instrument introduction section may have a distal end that is attached, and may be integrally formed, to the manifold and used for introducing an instrument into the artificial airway of the patient. A proximal end with an opening may also be present on the instrument introduction section. The proximal end is configured for releasable attachment to the instrument. The opening in the proximal end allows for the insertion of instruments into the instrument introduction section. A passageway exists from the opening in the proximal end to an opening in the distal end of the instrument introduction section. The instrument may be moved through this passageway. A valve may be located in the instrument introduction section and may have a closed position where the instrument may be at least substantially blocked from the artificial airway of the patient. The valve may have an open position that allows for the instrument to be advanced through the instrument introduction section.

Another exemplary embodiment of the present invention exists in a respiratory apparatus that may have a manifold configured for connection with an artificial airway of a patient. An instrument introduction section that has a distal end may be attached to the manifold. An instrument may be introduced through the instrument introduction section into the artificial airway of the patient. A proximal end is present on the instrument introduction section and may have an opening to allow for insertion of the instrument. The proximal end may be configured for releasable attachment to the instrument. A passageway is present from the opening in the proximal end to an opening in the distal end of the instrument introduction section. A valve may be present in the instrument introduction section and may at least substantially block the passageway when the valve is in a closed position. The valve may also have an open position that allows for the instrument to be advanced through the instrument introduction section. A cleaning section proximal from the valve may be provided in the instrument introduction section.

An irrigation port in communication with the cleaning section may also be present. The irrigation port may be configured for allowing fluid to be transferred into the cleaning section. Also, a plug may be engageable with the proximal end of the instrument introduction section. The plug may be adapted for isolating the passageway in the instrument introduction section from the environment. The passageway may be isolated through the closure of the opening in the proximal end of the instrument introduction section.

The present invention also provides for an alternative exemplary embodiment of the respiratory apparatus in accordance with the present invention. Here, a manifold is present and may be attached to a distal end of the instrument introduction section. The manifold may be in communication with the artificial airway of a patient. The manifold may have at least two proximal ports that are rotatable such that they are in axial alignment with a distal port of the manifold. No more than one of the proximal ports may be in axial alignment with the distal port of the manifold at any given time. Further, the distal end of the instrument introduction section may be attached to one of the proximal ports of the manifold. The instrument introduction section may be used for introducing an instrument into the artificial airway of the patient. The instrument introduction section may have a proximal end with an opening. The proximal end is configured for releasable attachment to the instrument. The opening in the proximal end may allow for insertion of the instrument into the instrument introduction section. A passageway exists from the opening from the proximal end to an opening in the distal end.

A single flap valve may be located in the instrument introduction section and may at least substantially block the passageway when in a closed position. The single flap valve may have an open position that allows the instrument to be advanced through instrument introduction section. A cleaning section may be defined by the instrument introduction section and may be proximal from the single flap valve. An irrigation port may also be present and in communication with the cleaning section. The irrigation port may be configured for allowing fluid to be transferred therethrough into the cleaning section. A cap configured to engage the proximal end of the instrument introduction section may also be present. The cap may have an opening that allows for insertion of the instrument into the opening in the proximal end of the instrument introduction section. A plug may be connected to the cap by a tether. The plug may be insertable into the opening in the cap to close the opening in the cap.

The present invention also provides for a respiratory apparatus as substantially described above where the instrument introduction section has a cleaning section. The cleaning section may be proximal from the valve when the valve is in the closed position. Further, an irrigation port may be in communication with the cleaning section and may be configured for allowing fluid to be transferred therethrough into the cleaning section.

The respiratory apparatus of the present invention may be used in conjunction with a variety of instruments. For example, the instrument may be a suction catheter, an endoscope, or a bronchoscope.

DETAILED DESCRIPTION

Reference will now be made in detail to embodiments of the invention, one or more examples of which are illustrated in the drawings. Each example is provided by way of explanation of the invention, and is not meant as a limitation of the invention. For example, features illustrated or described as part of one embodiment can be used with another embodiment to yield still a third embodiment. It is intended that the present invention include these and other modifications and variations.

As used herein, proximal refers generally to the direction towards a medical caregiver. Also, distal refers generally to the direction towards a patient.

The present invention provides for a respiratory apparatus that allows for instruments to be connected to and removed from the respiratory apparatus without having to disconnect the respiratory apparatus from a ventilation circuit. Further, the respiratory apparatus is configured to allow for cleaning and/or extended use of an instrument attached thereto.

Figure 1:
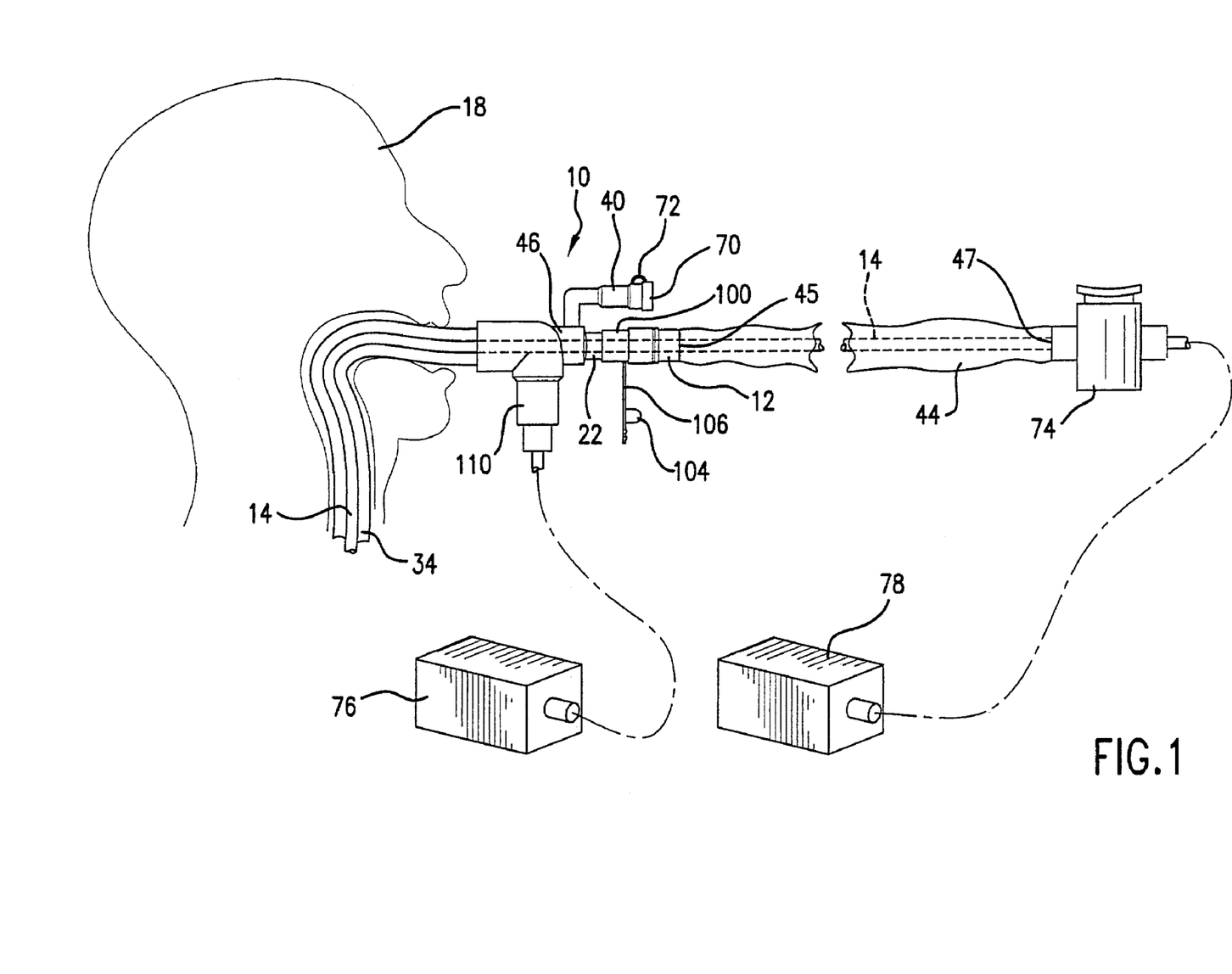
FIG. 1 is a perspective view of a respiratory apparatus in accordance with the present invention. A patient is shown having an artificial airway and a respiratory apparatus attached thereto with a suction catheter removably attached to the respiratory apparatus.

Referring to FIG. 1, the present invention may be used in conjunction with a variety of instruments that are placed into an artificial airway 34 of a patient 18. By way of example, the present invention is shown as being used in conjunction with a suction catheter 12 and related apparatus 10. A ventilator 76 may be in communication with the artificial airway 34 through a manifold 110. The ventilator 76 may provide air to and remove air from the lungs of the patient 18 through the artificial airway 34.

If the artificial airway 34 is left in the patient 18 for any substantial amount of time, respiratory secretions may build up in the lungs of the patient 18. As such, these secretions need to be removed in order to ensure that adequate lung ventilation of the patient 18 can be maintained. These secretions may be removed through use of the suction catheter 12. The suction catheter 12 has a tubular portion 14 that may be extended through the artificial airway 34 into the lungs of the patient 18. A vacuum source 78 may be in communication with the ventilating circuit, and more specifically in communication with the suction catheter 12. A medical caregiver may actuate a suction valve 74 thereby applying a vacuum pressure to the tubular portion 14 of the suction catheter 12. Upon doing so, respiratory secretions in the patient 18 and in the artificial airway 34 may be removed.

Respiratory secretions may sometimes remain on the tubular portion 14 of the suction catheter 12 or transfer onto other portions of the ventilator circuit. These respiratory secretions are undesirable in that they provide a breeding ground for pathogens and other harmful agents that may harm the patient 18. It is therefore the case that the suction catheter 12 and/or other components of the ventilation circuit may be cleaned in order to remove any residual respiratory secretions. However, in order to ensure a lower risk of contamination to the patient 18, it may be common practice to remove and replace the suction catheter 12 after some amount of set time has passed, for instance after 24 or 72 hours of use.

The suction catheter 12 is shown with a flexible plastic sleeve 44. The sleeve 44 may be present in order to contain and isolate respiratory secretions that accumulate on the tubular portion 14 of the suction catheter 12 as the tubular portion 14 is withdrawn from the ventilation circuit. The sleeve 44 may be provided on either end with sealing connections 45 and 47 that attach the sleeve 44 to the suction catheter 12.

In previous devices, the manifolds were permanently attached to the suction catheter 12 and were detachable from the artificial airway 34 so that a new suction catheter 12 could be incorporated into the ventilation circuit. This break in the ventilation circuit interrupted the flow of air to the patient 18 and increased the chances of ventilator associated complications. In the present invention, however, the suction catheter 12 may be removably attached to the respiratory apparatus 10. In this instance, upon removing the suction catheter 12, the respiratory apparatus 10 may remain in place and allow for communication between the ventilator 76 and the artificial airway 34. As such, air is still provided to the patient 18 during removal of the suction catheter 12. A new suction catheter 12 may be reattached to the instrument introduction section 22.

Figure 6:
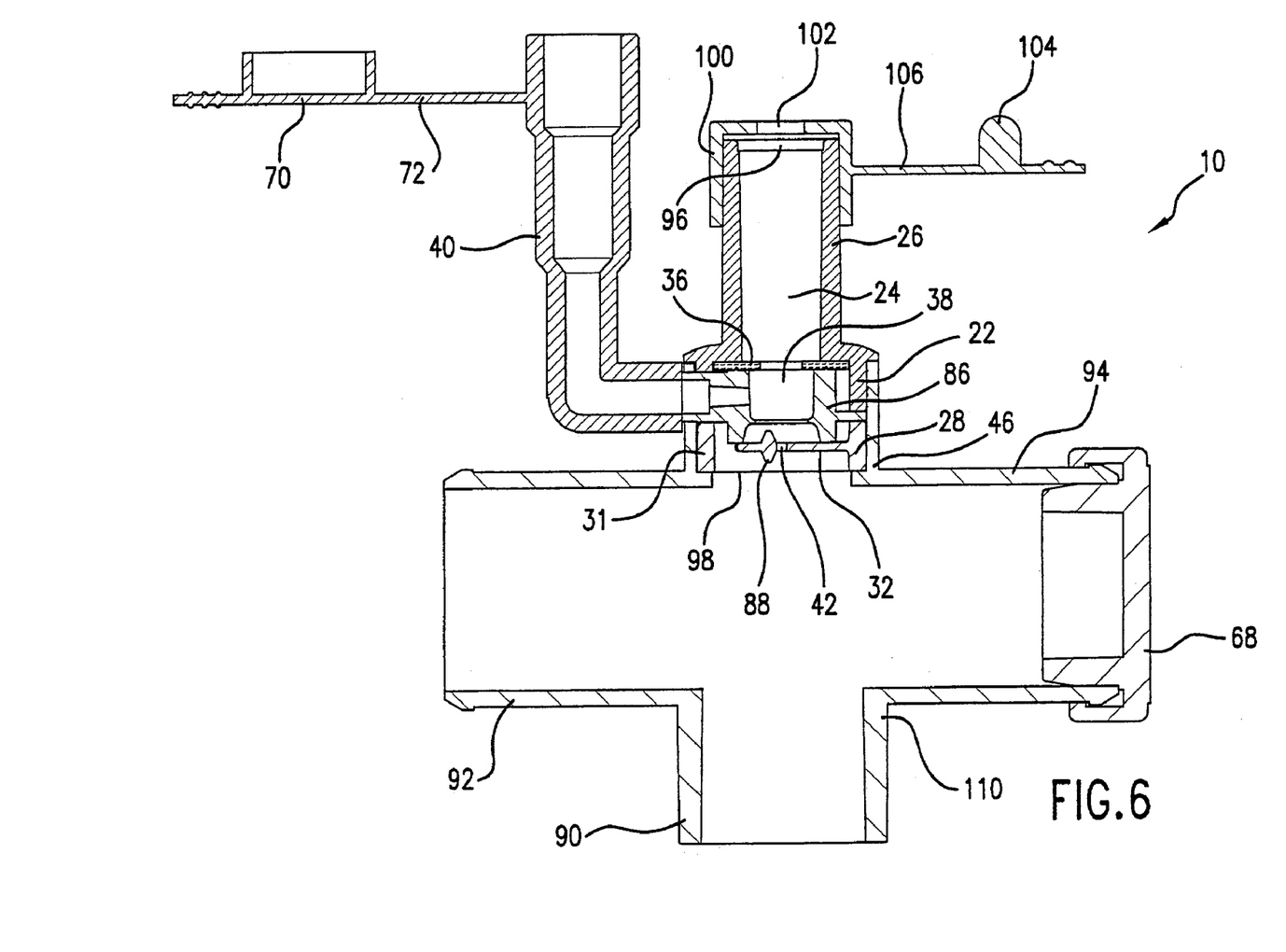
FIG. 6 is a cross sectional elevational view of a respiratory apparatus in accordance with the present invention. A T-piece manifold is included in the respiratory apparatus.

The respiratory apparatus 10 in accordance with the present invention may be provided with a variety of manifolds 110. For instance, in one exemplary embodiment of the present invention as shown in FIG. 6, the respiratory apparatus 10 may be used with a T-piece manifold 110. A port 90 may be present and may be attached to the artificial airway 34 (FIG. 1). The port 90 therefore allows for communication between the manifold 110 and the artificial airway 34. Air from the ventilator 76 (FIG. 1) may be provided to and removed from the manifold 110 through a port 92. The port 92 may be attached to a pair of ventilation tubes via a connector (not shown). An additional port 94 on the manifold 110 may be provided opposite the port 92. The port 94 is typically covered with a cap 68 which is removed when "blow-by" is desired to wean the patient 18 (FIG. 1) from forced ventilation. An additional port 46 may be configured to engage the instrument introduction section 22 of the respiratory apparatus 10.

Figure 8:
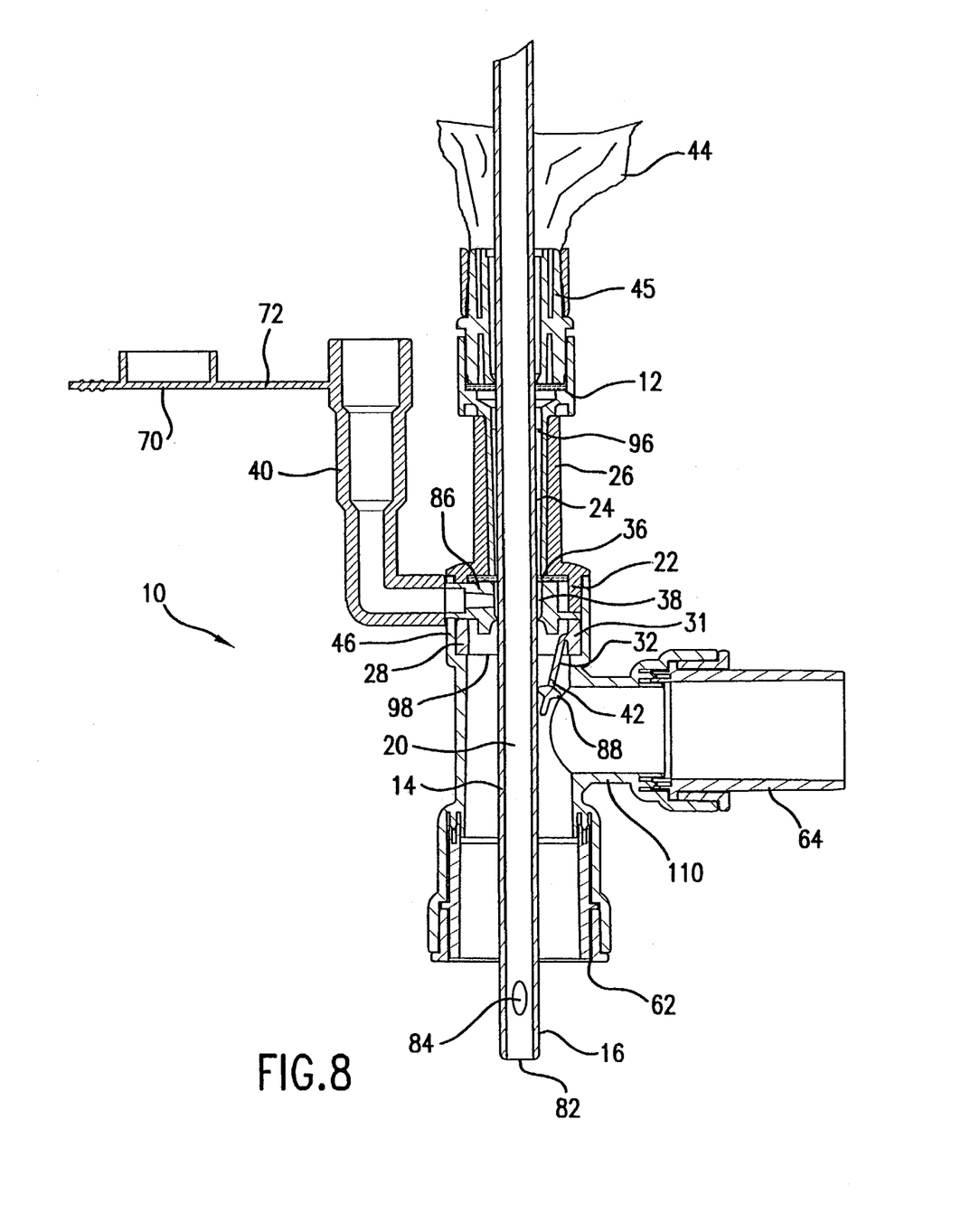
FIG. 8 is a cross sectional elevational view of a respiratory apparatus in accordance with the present invention. A suction catheter is attached to the respiratory apparatus, and a tubular portion of the suction catheter is shown as being advanced through the instrument introduction section and the manifold of the respiratory apparatus.

The respiratory apparatus 10 is shown in FIG. 8 having the suction catheter 12 advanced therethrough. The respiratory apparatus 10 includes the instrument introduction section 22 to which the instrument such as the suction catheter 12 may be attached in any suitable manner. The instrument introduction section 22 may have a passageway 24 extending therethrough. A tubular portion 14 of the suction catheter 12 may be advanced through the passageway 24, through an opening 98 in the distal end 28 and into the manifold 110, and eventually advanced into the artificial airway 34 (FIG. 1). Upon retraction of the tubular portion 14 from the patient 18, respiratory secretions may be present on the surface of the tubular portion 14. A wiper seal 36 may be provided in the instrument introduction section 22. The wiper seal 36 may be a resilient member having an aperture therethrough that allows for the tubular portion 14 to pass. The wiper seal 36 desirably tightly engages the tubular portion 14 as the tubular portion 14 is retracted from the artificial airway 34 to a position proximal from the wiper seal 36. Respiratory secretions present on the surface of the tubular portion 14 may be removed by contact with the wiper seal 36.

The instrument introduction section 22 may also be provided with a cleaning section 38. In one exemplary embodiment, the cleaning section 38 may be defined by a cleaning section member 86. Additionally or alternatively, the cleaning section 38 may be defined on one end by a valve 32. Further, the cleaning section 38 may alternatively be defined by any portion of the instrument introduction section 22. The valve 32 is shown in a closed position in FIG. 2 and in an open position in FIG. 8. The valve 32 shown in FIG. 8 is a single flap that is hingedly attached to an annular ring 3 housed within the instrument introduction attachment section 22. The hinge on the valve 32 may provide both a bias force and a pivoting location. Use of such a valve 32 is disclosed in U.S. Pat. 6,227,200 B1 issued to Crump et al., the entire disclosure of which is incorporated by reference herein in its entirety for all purposes.

As can be seen in FIG. 8, the tubular portion 14 of the suction catheter 12 may have a distal end 16 with a distal opening 82. A lumen 20 may extend through the tubular portion 14 and allows for respiratory secretions and other fluids to be transferred through the distal opening 82 and into the lumen 20 by the vacuum source 78 (shown in FIG. 1). The tubular portion 14 of the suction catheter 12 may be cleaned by positioning the distal end 16 of the suction catheter 12 either against the valve 32 or within the cleaning section 38. Upon so positioning, a vacuum can be effected upon the lumen 20 and lavage or other cleaning solution may be injected into the cleaning section 38. Application of the vacuum can cause the valve 32 to be forced against the distal end 16 of the tubular portion 14. However, in other exemplary embodiments, the valve 32 may be biased with enough force to close and seal against the distal end 16 without application of suction force. In one exemplary embodiment of the present invention, the valve 32 may at least substantially block the passageway 24 when in a closed position. However, it is to be understood that injection of lavage or other cleaning solutions and/or application of a vacuum may be performed in instances not associated with cleaning of the tubular portion 14 of the suction catheter 12.

Although described as contacting the distal end 16 of the suction catheter 12, in certain exemplary embodiments of the present invention, the valve 32 need not contact the distal end 16 of the tubular portion 14 in order to effectively clean the tubular portion 14. For instance, the valve 32 may be urged against the cleaning section member 86 during cleaning of the tubular portion 14.

The tubular portion 14 may also be provided with at least one side opening 84. This arrangement allows for a turbulent flow to be established within the cleaning section 38 during suctioning causing the lavage solution to break up and remove any respiratory secretions present on the tubular portion 14. Respiratory secretions may be removed through the side opening 84 and/or the distal opening 82. The valve 32 may be provided with an aperture 42 therethrough. The presence of the aperture 42 may help to establish a more desirable turbulent fluid flow within the cleaning section 38. In one exemplary embodiment of the present invention, the aperture 42 is about 0.03 inches in diameter.

An irrigation port 40 is shown attached to the instrument introduction section 22 in order to allow for the injection of the lavage solution. A container (not shown) holding the lavage solution may have an outlet inserted into the irrigation port 40. Lavage may then be dispensed from this container into the irrigation port 40 which may be in communication with the cleaning section 38. The irrigation port 40 may also be provided with an irrigation cap 70 that may be connected to the irrigation port 40 by way of a tether 72. The irrigation cap 70 may be placed onto the irrigation port 40 in order to close the irrigation port 40 when not in use.

In certain exemplary embodiments of the present invention, the cleaning section member 86 may be configured such that a small amount of space is present between the tubular portion 14 of the suction catheter 12 and the cleaning section member 86. In certain exemplary embodiments of the present invention, this space may be between about 0.005 and about 0.015 inches. This space provides two advantages. First, if lavage is needed to be provided to the patient 18, injection of lavage through the irrigation port 40 and then into the cleaning section 38 causes a stream of lavage solution to be directed out of the manifold 110 and into the patient 18. Second, as the tubular portion 14 is withdrawn, the close proximity between the tubular portion 14 and the cleaning section member 86 may help to wipe any heavy layers of respiratory secretions from the outside of the tubular portion 14 of the suction catheter 12.

Employment of the valve 32 is advantageous in that the tubular portion 14 of the suction catheter 12 may be cleaned without causing a pressure loss to the ventilation circuit. This is because the valve 32 substantially isolates the portion of the respiratory apparatus 10 proximal the valve 32 from the remainder of the ventilation circuit. In one exemplary embodiment of the present invention, the valve 32 may be provided with one or more projections 88. FIG. 8 shows the respiratory apparatus 10 where the manifold 110 is an elbow manifold that has swiveling ports 62 and 64. The tubular portion 14 of the suction catheter 12 is shown as being advanced through the instrument introduction section 22, the manifold 110, and out of the port 62 eventually entering the artificial airway 34 of the patient 18 (FIG. 1). The valve 32 may be opened by insertion of the tubular portion 14 through the instrument introduction section 22. The projection 88 may be configured to minimize valve 32 contact with the surface of the tubular portion 14. This contact helps to reduce contamination of respiratory secretions from the tubular portion 14 onto the valve 32 and related components due to the minimized contact afforded by the projections 88. Additionally, this contact in certain exemplary embodiments may help to ensure the structural integrity of the valve 32 and prevent any unnecessary bending or stress on the valve 32.

In one exemplary embodiment of the present invention, the valve 32 may be biased towards the closed position. Although shown in FIG. 8 as being attached to an annular ring 31, the valve 32 may be attached directly onto a wall of the instrument introduction section 22. The valve 32 may be configured to be closed once the tubular portion 14 is positioned proximally from the valve 32, or alternatively the valve 32 may be configured to be closed upon the proximal positioning of the tubular portion 14 from the valve 32 and application of vacuum through the lumen 20 in order to draw the valve 32 into a sealed, closed position.

The valve 32 need not be a single flap. It is to be understood that the configuration of the valve 32 shown in the drawings is only a desired embodiment, and other configurations of the valve 32 are possible in accordance with the present invention. For instance, the valve 32 may be two, three or more flaps that are biased towards a closed position and opened by insertion of the tubular portion 14 of the suction catheter 12 through the instrument introduction section 22.

Figure 2:
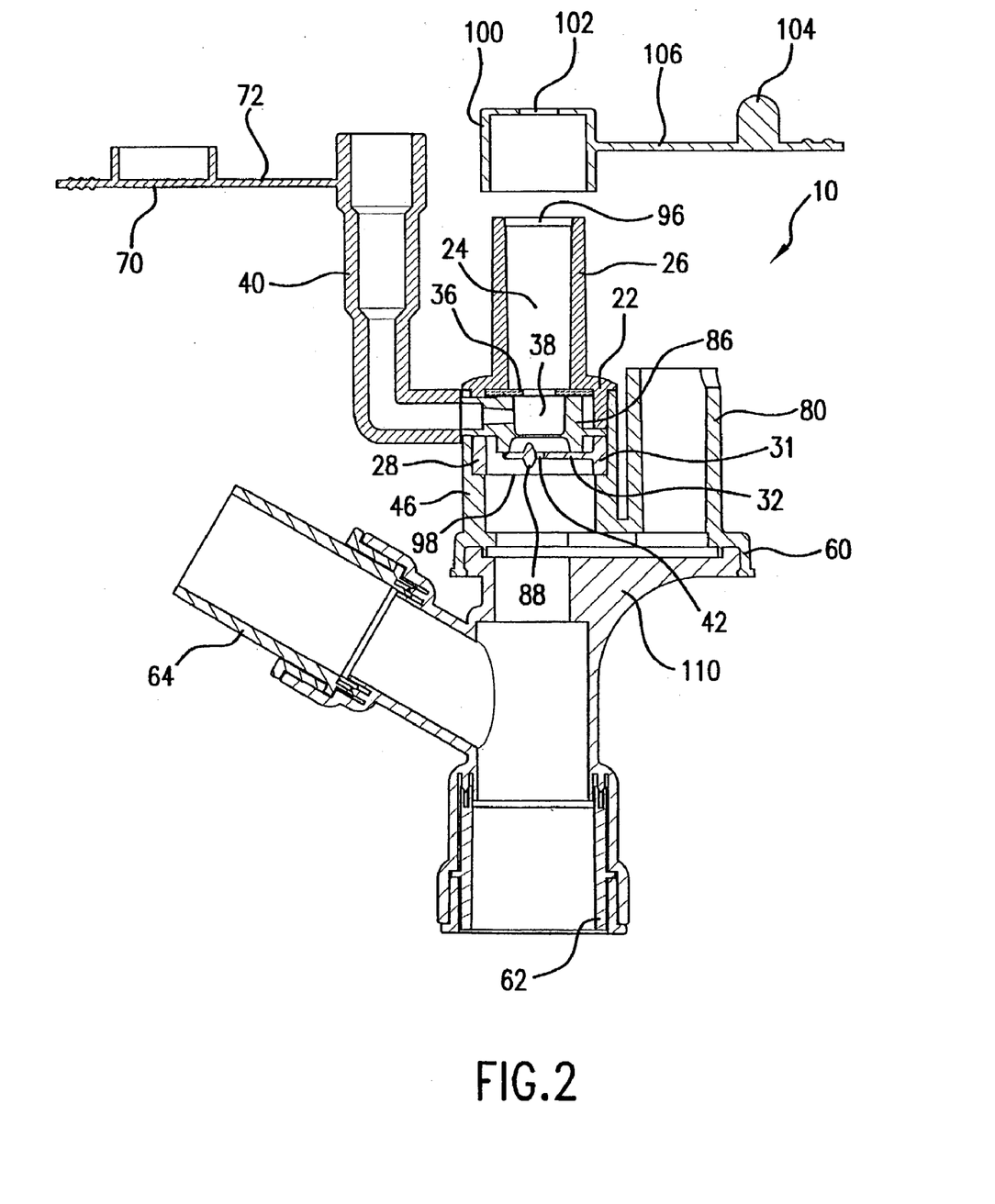
FIG. 2 is a cross sectional elevational view of a respiratory apparatus in accordance with the present invention. A manifold is included that is rotatable so that one of two proximal ports may be in axial alignment with a distal port of the manifold.

Referring to FIG. 2, the instrument introduction section 22 is provided with a proximal end 26 and a distal end 28. The proximal end 26 may be releasably attached to the suction catheter 12 through a variety of means commonly known in the art. For instance, these two components may be friction fit to one another, clamped to one another, releasably attached through a barbed connection, or connected through a threaded engagement. The suction catheter 12 may therefore be releasably attached to the proximal end 26 in any suitable manner known to those skilled in the art.

The distal end 28 of the instrument introduction section 22 may be permanently attached to a port 46 on the manifold 110. Engagement of the distal end 28 and the port 46 is shown in FIG. 2. In this exemplary embodiment, the distal end 28 is attached to the port 46. The two parts are force fit onto one another during assembly. They may be heat treated in order to provide for a more secure attachment. Alternatively the two components may be connected via sonic welding, with an adhesive, or may be formed as one integral piece in other exemplary embodiments.

The manifold 110 shown in FIG. 2 is provided with an additional port 80 onto which the instrument introduction section 22 of the respiratory apparatus 10 may be attached in other exemplary embodiments. Additionally, in yet other exemplary embodiments of the present invention, two instrument introduction sections 22 may be employed such that their respective distal ends 28 of their respective instrument introduction sections 22 are attached to the port 46 and the port 80.

Figure 7:
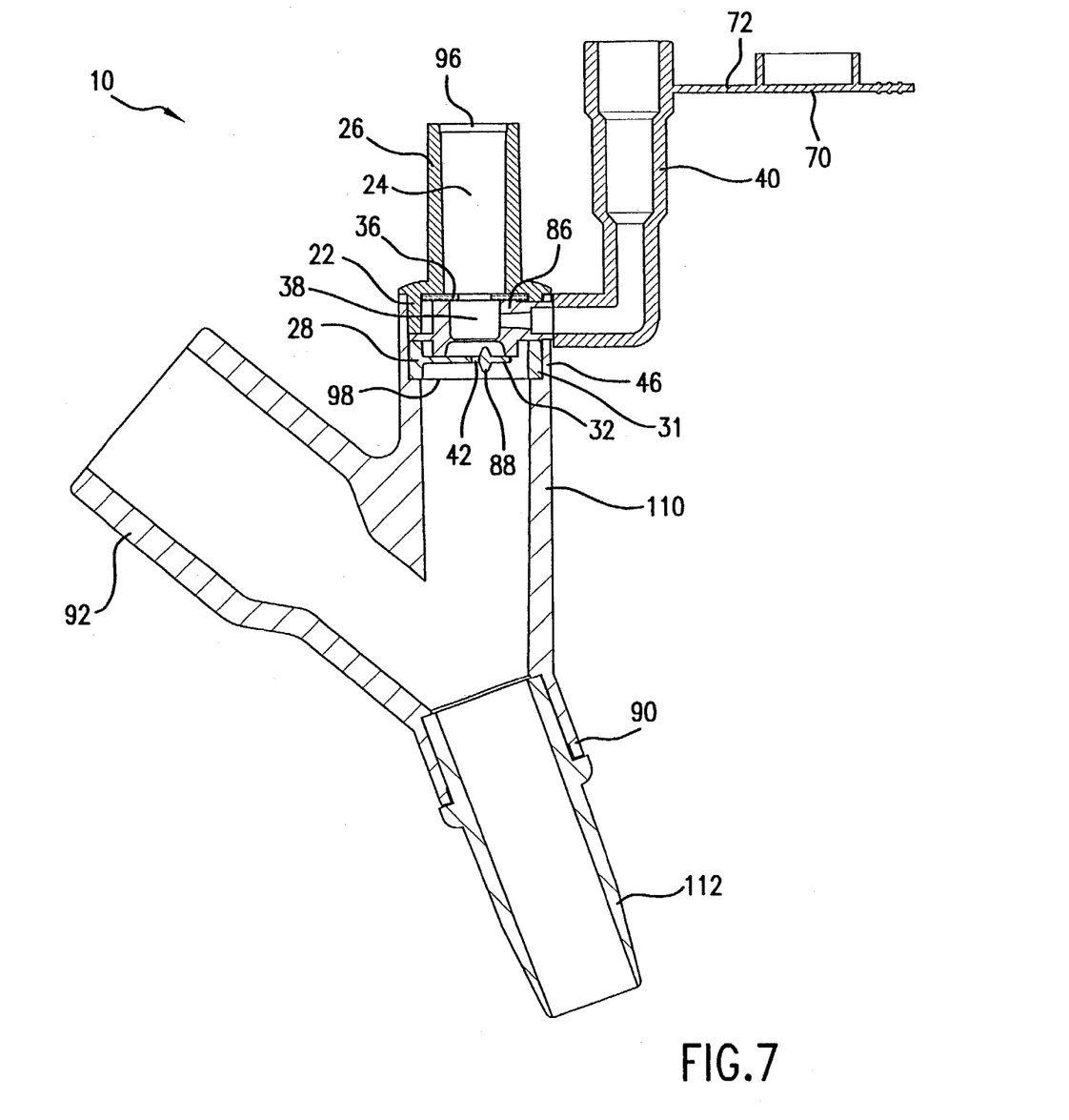
FIG. 7 is a cross sectional elevational view of a respiratory apparatus in accordance with the present invention. The respiratory apparatus includes a neonate Y-manifold.

The respiratory apparatus 10 is shown as being provided with a cap 100 placed on the proximal end 26 of the instrument introduction section 22. An opening 102 in the cap 100 may be provided through which the suction catheter 12 may be passed prior to being passed through an opening 96 in the proximal end 26 of the instrument introduction section 22. The opening 102 may be sized so that various instruments may be used in conjunction with the respiratory apparatus 10. The opening 102 may be closed by a plug 104 that is connected to the cap 100 by way of a tether 106. FIG. 5 shows an exemplary embodiment where the plug 104 is inserted into the opening 102 (FIG. 4), hence acting to close the opening 96 in the proximal end 26 of the instrument introduction section 22. Closing off the opening 96 may help to prevent contamination of the respiratory apparatus 10 by contaminants in the environment when instruments are not being used in conjunction with the respiratory apparatus 10. Additionally, during mechanical ventilation of the patient 18, it is advantageous to close the opening 96 so that positive end expiratory pressure can be maintained in the ventilation circuit. Although it is also possible to maintain the positive end expiratory pressure through the use of the valve 32, the use of the plug 104 to close off the proximal end 26 provides for an alternative or supplemental way of maintaining the positive end expiratory pressure. As suggested above, a cap 100 need not be provided on the respiratory apparatus 10. For instance, FIGS. 7 and 8 illustrated exemplary embodiments that do not have such a cap 100 present.

Figure 10:
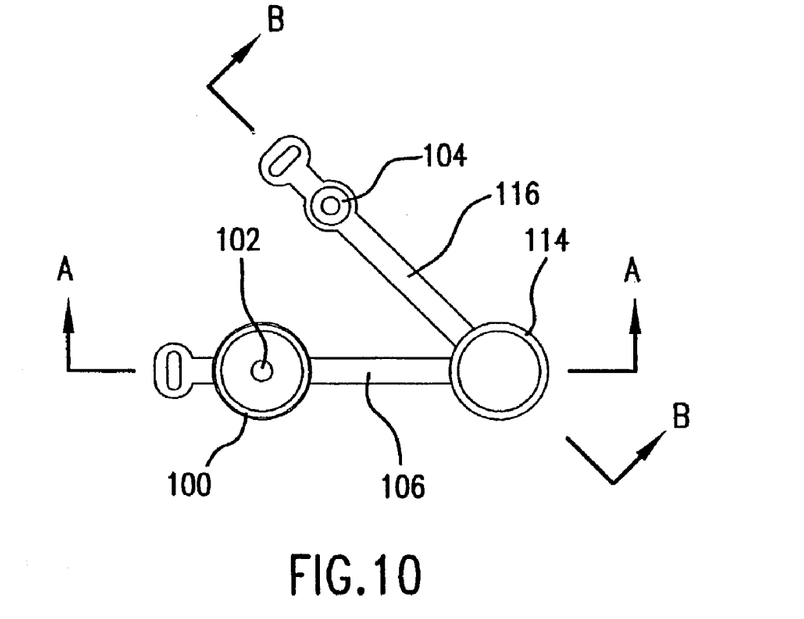
FIG. 10 is a top plan view of an alternative cap and plug assembly in accordance with the present invention.
Figure 11:
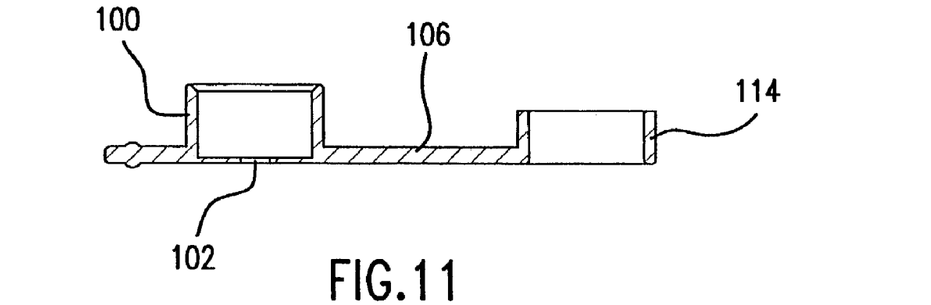
FIG. 11 is a cross sectional view taken along line A-A in FIG. 10.
Figure 12:
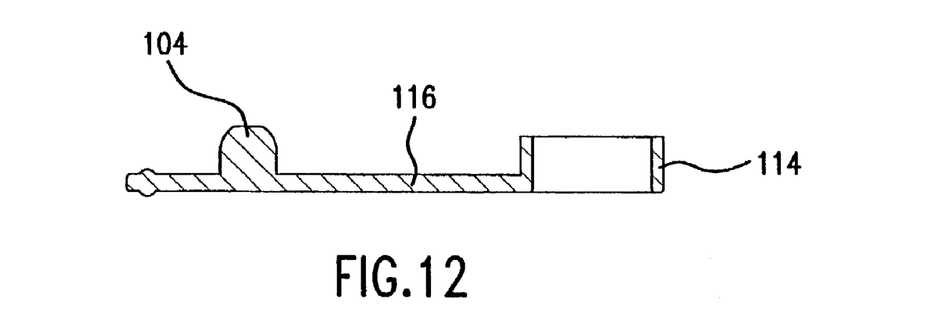
FIG. 12 is a cross sectional view taken along line B-B in FIG. 10.

FIGS. 10-12 show an alternative arrangement of the cap 100 and the plug 104 in accordance with an exemplary embodiment of the present invention. Here, an attachment member 114 may be present and may be attached to any component of the respiratory apparatus 10, for example the proximal end 26. The cap 100 is shown as being connected to the attachment member 114 by way of the tether 106, while the plug 104 is connected to the attachment member 114 by a separate plug tether 116. The cap 100 may be placed over a portion of the respiratory apparatus 10, for instance the opening 96. Further, when desired, the plug 104 may be placed within the opening 102 in the cap 100.

As shown in FIG. 2, the port 46 is in axial alignment with the swiveling port 62 that may be further attached to the artificial airway 34 (FIG. 1). This alignment may help to reduce contamination due to the fact that the suction catheter 12 (FIG. 1) during withdrawal from the patient 18 (FIG. 1) does not have to pass around bends or over other objects in order to be withdrawn into the instrument introduction section 22 proximate to the valve 32. In effect, this arrangement is a "straight shot" that reduces the chances of respiratory secretions being scrapped off of the tubular portion 14 of the suction catheter 12 and being deposited onto a bend or other obstacle in the respiratory apparatus 10. The rotating member 60 is provided on the manifold 110 and may allow for the rotation of the ports 46 and 80 such that port 80 may be axially aligned with the swiveling port 62, hence moving port 46 out of axial alignment. The suction catheter 12 inserted through the port 80 does not have to be moved over a bend or against an obstacle in order to be transferred through the respiratory apparatus 10. Only one of the ports 46 and 80 will be an axial alignment with the swiveling port 62 at any one given time. This type of manifold 110 is disclosed in U.S. Pat. No. 5,735,271 to Lorenzen et al., the entire disclosure of which is incorporated by reference herein in its entirety for all purposes. However, it is to be understood that the configuration of the manifold 110 shown in FIG. 2 is only an exemplary embodiment of the present invention, and the present invention is not limited to having the manifold 110 have rotating ports such that they may be aligned with a distal port of the manifold 110. The respiratory apparatus 10 in accordance with the present invention may be provided with manifolds 110 of any configuration known in the art.

The manifold 110 may have another swiveling port 64 located thereon that may be in communication with the ventilator 76 (FIG. 1). These two ports 62 and 64 are provided with a swiveling feature so that the tubing and/or structure connected to them more easily moves when various parts of the ventilation circuit are manipulated or moved. This helps to reduce stress imparted onto the patient 18 brought about by movement of the ventilation circuit. The swiveling ports 62 and 64 may be constructed, for instance, as those disclosed in U.S. Pat. No. 5,694,922 to Palmer, the entire disclosure of which is incorporated by reference herein in its entirety for all purposes.

Figure 3:
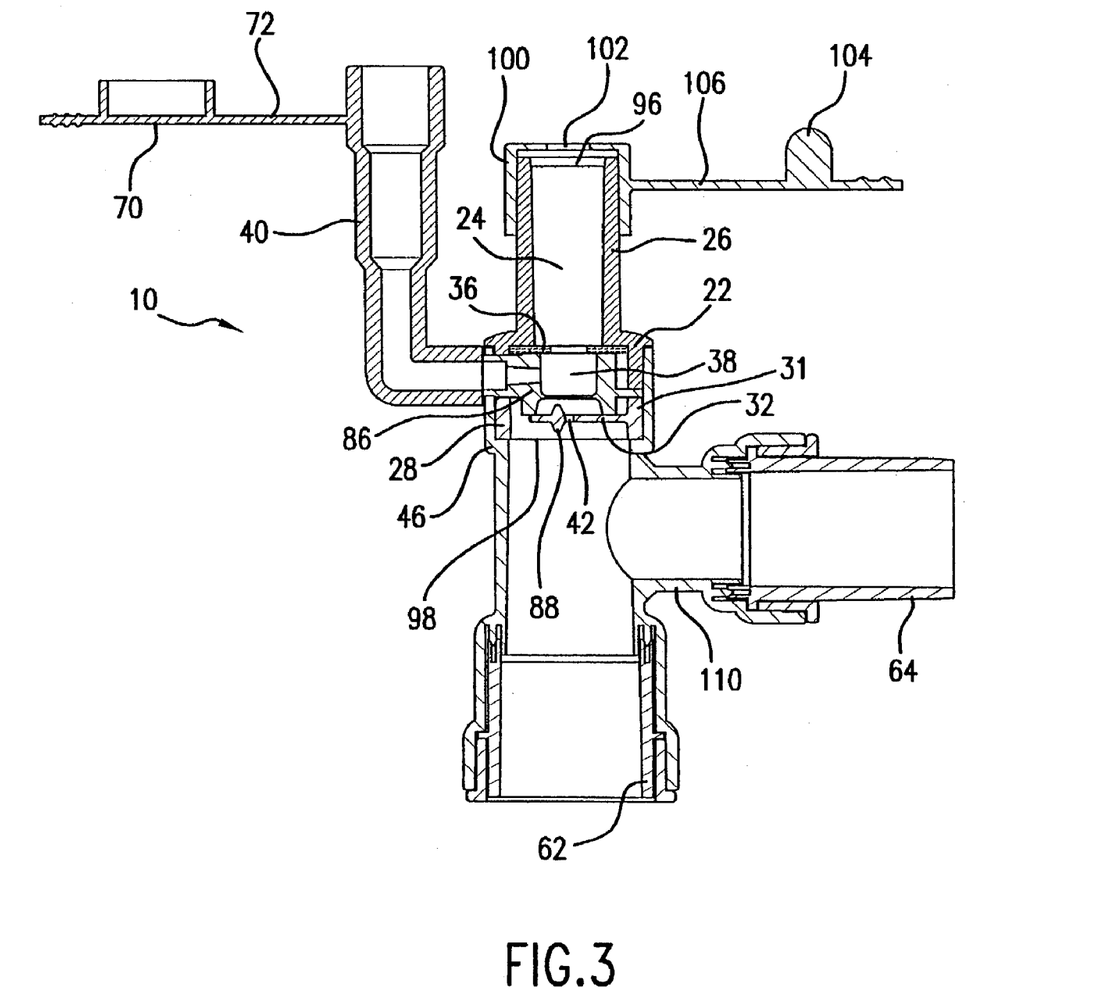
FIG. 3 is a cross sectional elevational view of a respiratory apparatus in accordance with the present invention. The respiratory apparatus includes an elbow manifold that has swiveling ports.

Another exemplary embodiment of the present invention is shown in FIG. 3. Here, the respiratory apparatus 10 may be substantially similar to the respiratory apparatus 10 described above with respect to the exemplary embodiment shown in FIG. 2. However, the manifold 110 is in this instance may be an elbow manifold that has a pair of swiveling ports 62 and 64. The manifold 110 is not shown as having a rotating member, and as such, the port 46 is stationary with respect to the rest of the manifold 110.

Figure 4:
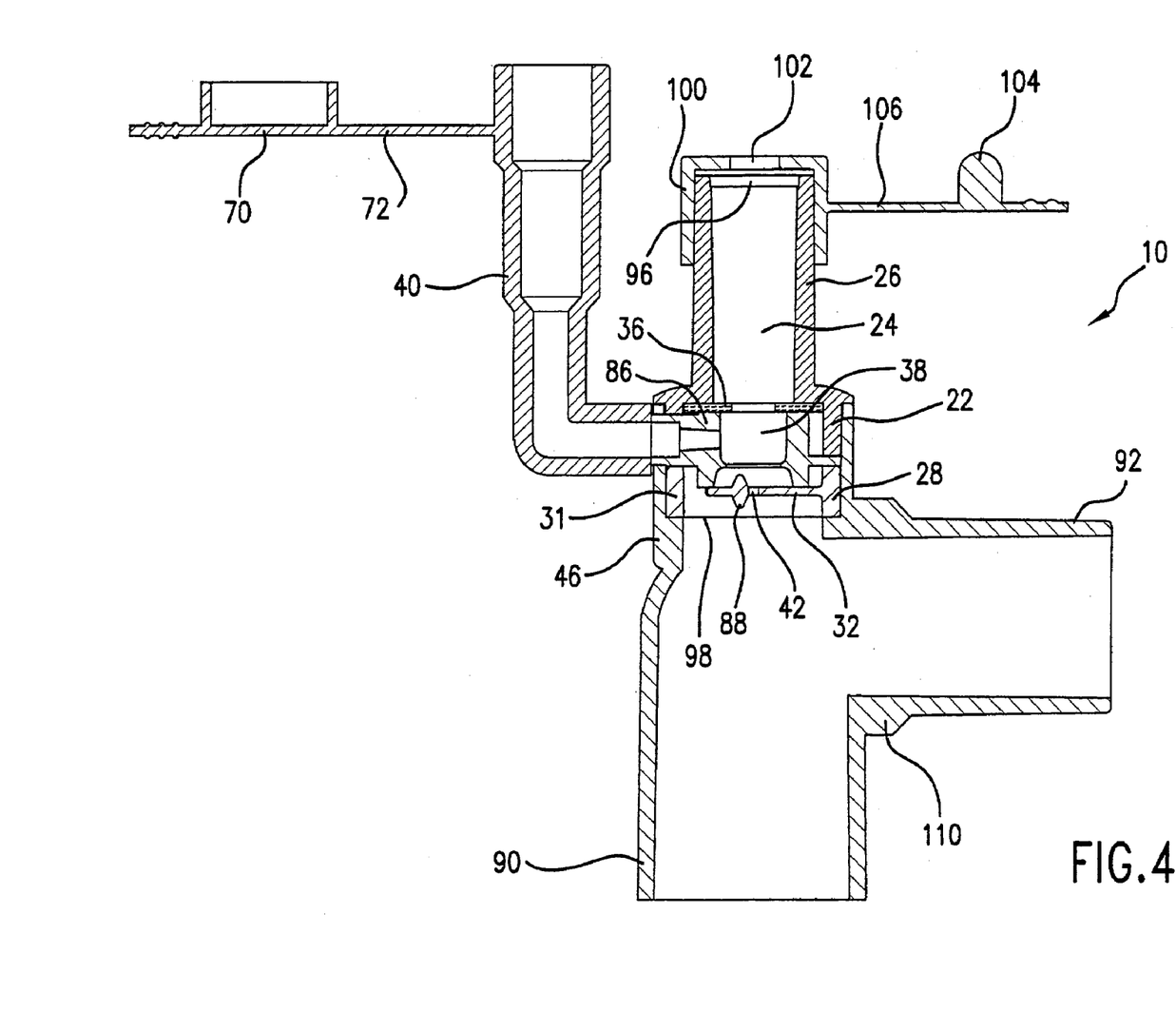
FIG. 4 is a cross sectional elevational view of a respiratory apparatus in accordance with the present invention. The respiratory apparatus includes an elbow manifold that does not have swiveling ports.
Figure 5:
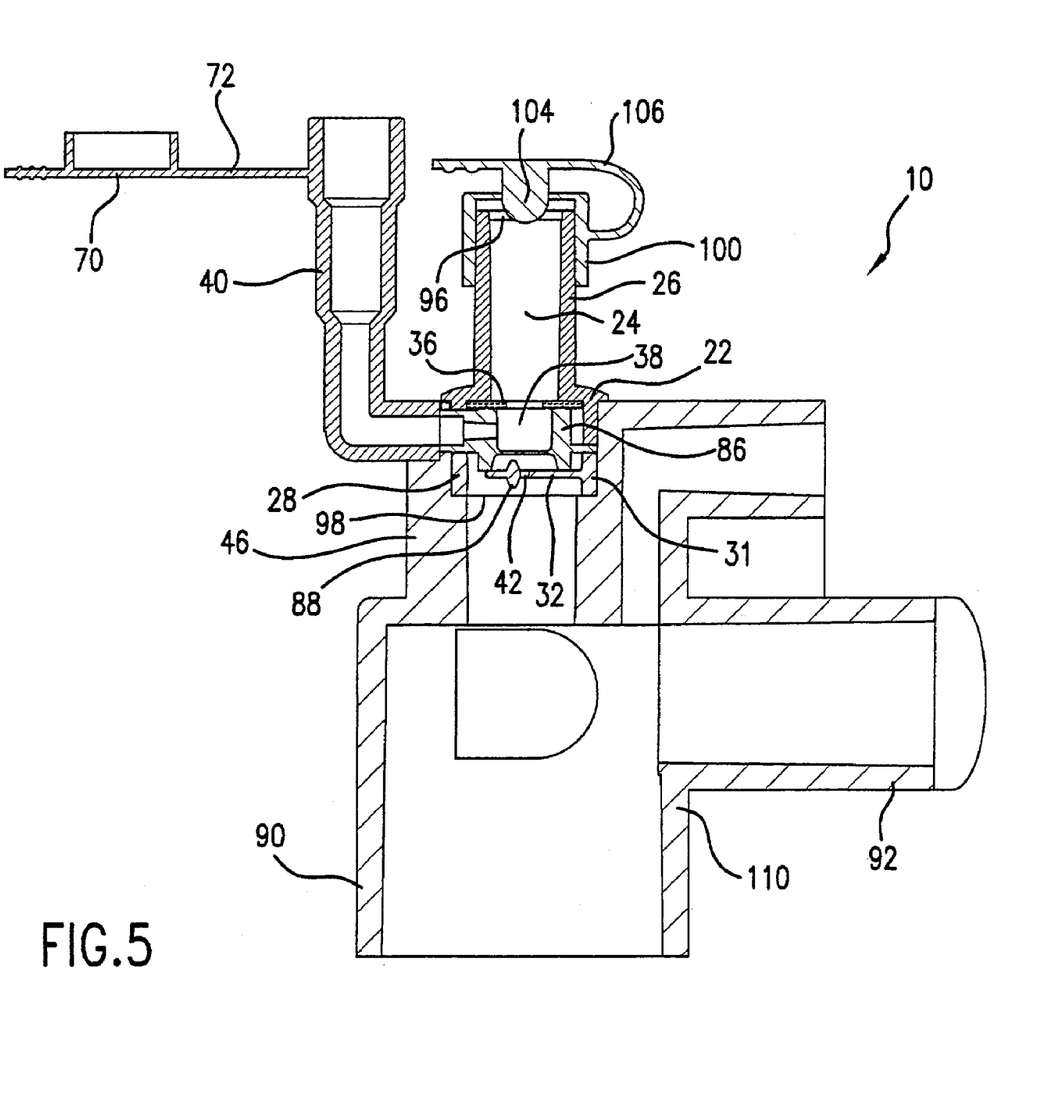
FIG. 5 is a cross sectional elevational view of a respiratory apparatus in accordance with the present invention. A plug is shown inserted into an opening in an instrument introduction section of the respiratory apparatus.

Yet another exemplary embodiment of the present invention is disclosed in FIG. 4. Here, the manifold 110 is an elbow manifold that has ports 90 and 92 located thereon that do not include the swiveling feature. These two ports form part of the ventilation circuit that provides air to and from the patient 18 (FIG. 1) through the port 90 and provides air to and from the ventilator 76 (FIG. 1) through the port 92.

Another manifold 110 used in accordance with another exemplary embodiment of the present invention is shown in FIG. 5. Here, the manifold 110 is a neonate manifold having a plurality of ports. Besides port 46, other ports are present, two ports in addition to port 46 are labeled. The port 92 may provide access to and from the ventilator 76 (FIG. 1), and the port 90 may provide access to and from the artificial airway 34 (FIG. 1) of the patient 18 (FIG. 1). The port 46 may be attached to the distal end 28 of the instrument introduction section 22.

An additional exemplary embodiment of the present invention is shown in FIG. 7. Here, the respiratory apparatus 10 may include a manifold 110 that is a neonate Y-manifold. The distal end 28 may be connected to the port 46 on the manifold 110. Ports 90 and 92 of the manifold 110 allow for communication between the ventilator 76 (FIG. 1) and the artificial airway 34 (FIG. 1). A tapered adaptor 112 may be retained within the port 90 in order to allow for connection of the respiratory apparatus 10 to tubing or other components of the respiratory circuit. The tapered adaptor 112 may or may not be permanently attached to the port 90. Alternatively, the manifold 110 itself may be tapered, hence eliminating the need for the tapered adaptor 112 in other exemplary embodiments of the present invention.

In accordance with the present invention, the respiratory apparatus 10 may be sized such that it may be attached to a variety of different artificial airways 34. Additionally, the respiratory apparatus 10 may be sized with different sized proximal ends 26, valves 32, and wiper seals 36, etc., so that different sized instruments can be used with the respiratory apparatus 10. As such, the present invention includes various sizes and configurations of the respiratory apparatus 10. The examples of which described herein are only exemplary embodiments of the present invention and do not limit the present invention.

Figure 9:
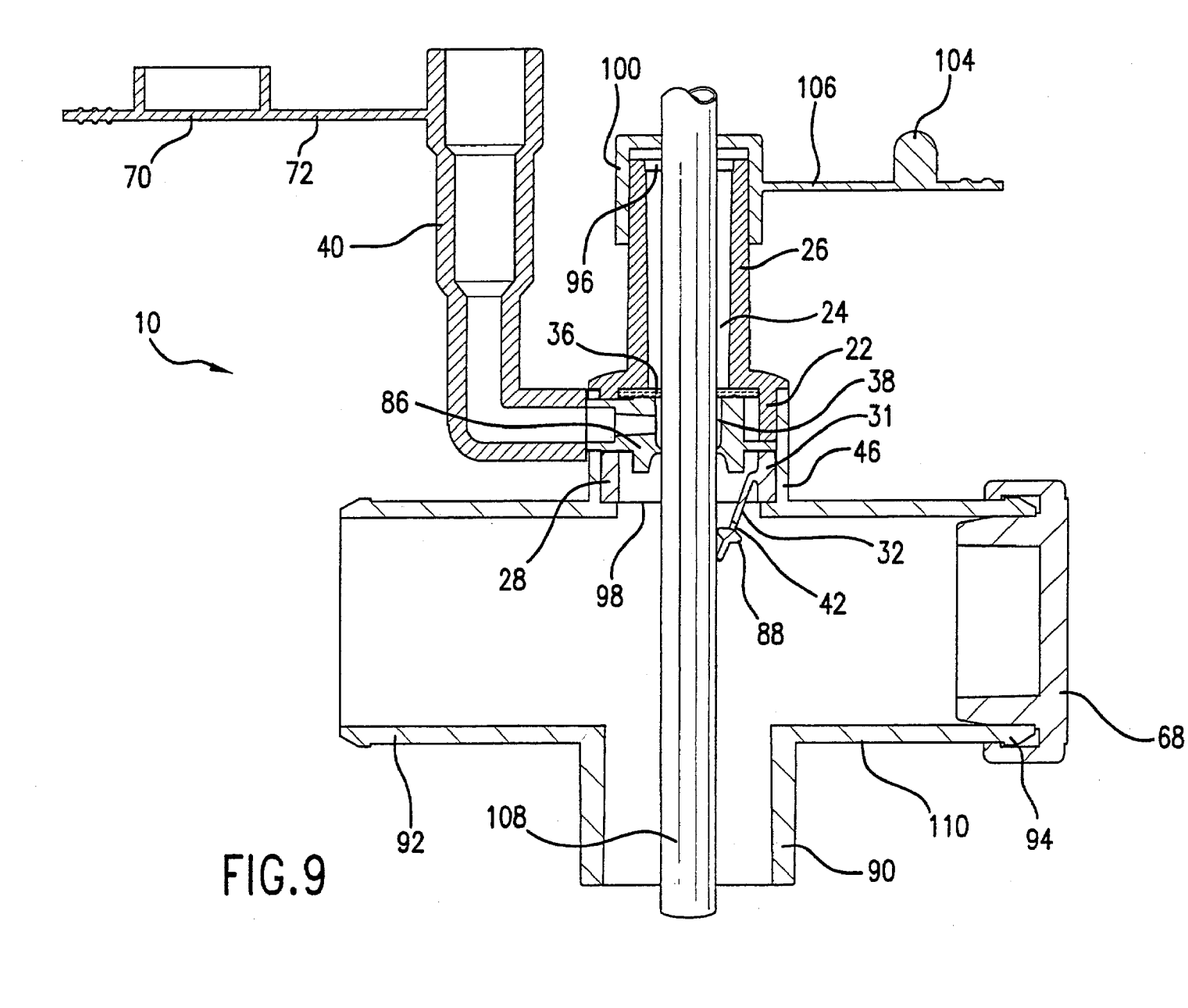
FIG. 9 is a cross sectional elevational view of a respiratory apparatus in accordance with the present invention. A bronchoscope is shown as being advanced through a cap, an instrument introduction section, and a manifold of the respiratory apparatus.

Although the present invention has been described as being used in connection with a suction catheter 12, it is to be understood that the instrument may be something other than a suction catheter 12 in accordance with other exemplary embodiments of the present invention. For instance, FIG. 9 shows the respiratory apparatus 10 having a bronchoscope 108 inserted therethrough. The bronchoscope 108 may be inserted through the passageway 24, into the manifold 110, and into the artificial airway 34 (FIG. 1) of the patient 18 (FIG. 1). Also, the bronchoscope 108 may be cleaned in much the same way as describe above with respect to the suction catheter 12 (FIG. 1). For instance, the tip of the bronchoscope 108 may be positioned proximate to the valve 32, lavage solution may be injected into the cleaning section 38, and suction may be applied through the bronchoscope 108 so that respiratory sections are removed from the surface of the bronchoscope 108. Alternatively, other instruments such as an endoscope may be used in conjunction with the respiratory apparatus 10. The respiratory apparatus 10 therefore allows for different instruments to be placed therethrough and to be able to be cleaned by insertion of lavage solution and/or application of suction. The respiratory apparatus 10 allows for different types of instruments to be inserted into the artificial airway 34 (FIG. 1) without having to disconnect the manifold 110 and cause the aforementioned interruption in ventilation air to the patient. Additionally, the valve 32 can act to maintain positive end expiratory pressure when in the closed position. It is to be understood that the present invention is not limited to a respiratory apparatus 10 that is used in conjunction with a suction catheter 12, but may be used with any instrument that is to be inserted into the artificial airway 34 (FIG. 1).

Allowing for the instrument, such as the suction catheter 12, to be releasably attachable to the respiratory apparatus 10 allows for other uses of the respiratory apparatus 10 without interruption of the ventilation circuit. Therefore, different types of instruments may be interchanged with the respiratory apparatus 10. The respiratory apparatus 10 may allow for the airway pressure of the ventilation circuit to be measured. Another use for the respiratory apparatus 10 is in providing access to the artificial airway 34 such that oxygen and insufflation therapy can be administered to the patient 18. Also, the respiratory apparatus 10 may have a filtering device (not shown) attached to the proximal end 26 so that the patient 18 may be weaned from artificial breathing through the use of the ventilator 76. The respiratory apparatus 10 therefore may be designed to be used with various instruments and may be used in conjunction with various medical procedures that are preformed on the patient 18 without breaking the ventilation circuit and suffering the disadvantages associated therewith.

It should be understood that the present invention includes various modifications that can be made to the embodiments of the respiratory apparatus described herein as come within the scope of the appended claims and their equivalents.

What is claimed is:

1. A respiratory apparatus, comprising:
    a manifold configured for connection in communication with an artificial airway of a patient;
    an instrument introduction section comprising:
        a distal end attached to the manifold for introducing an instrument into the artificial airway of the patient;
        a proximal end with an opening, the proximal end configured for releasable attachment to the instrument, the opening in the proximal end allowing for insertion of the instrument into the instrument introduction section; and
        a passageway from the opening in the proximal end to an opening in the distal end, wherein the instrument is movable through the passageway; and
    a valve located in the instrument introduction section, the valve having a closed position in which the instrument is at least substantially blocked from the artificial airway of the patient, the valve having an open position that allows the instrument to be advanced through the instrument introduction section,
    wherein the manifold has at least two proximal ports rotatable so as to be in axial alignment with a distal port of the manifold, no more than one of the proximal ports being in axial alignment with the distal port of the manifold at any one time, and the distal end of the instrument introduction section attachable to one of the proximal ports of the manifold.

2. The respiratory apparatus of claim 1, further comprising a positive end expiratory pressure cap located on the proximal end of the instrument introduction section.

3. The respiratory apparatus of claim 1, further comprising:
    a cap configured to engage the proximal end of the instrument introduction section, the cap having an opening that allows for insertion of the instrument into the opening in the proximal end of the instrument introduction section.

4. The respiratory apparatus of claim 1, further comprising a plug configured to engage the proximal end of the instrument introduction section to close the opening in the proximal end of the instrument introduction section.

5. The respiratory apparatus of claim 1, wherein the instrument is selected from the group consisting of a suction catheter, an endoscope, and a bronchoscope.

6. The respiratory apparatus of claim 1, wherein the instrument is a suction catheter, the proximal end of the instrument introduction section configured for releasable attachment with the suction catheter.

7. The respiratory apparatus of claim 1, further comprising a wiper seal located in the instrument introduction section proximal from the valve.

8. The respiratory apparatus of claim 1, further comprising:
    a cleaning section located in the instrument introduction section proximal from the valve; and
    an irrigation port in communication with the cleaning section, the irrigation port configured for allowing fluid to be transferred therethrough into the cleaning section.

9. The respiratory apparatus of claim 1, wherein the valve is a single flap.

10. The respiratory apparatus of claim 9, wherein the single flap has an aperture therethrough, the single flap adapted to be opened by insertion of the instrument through the instrument introduction section.

11. The respiratory apparatus of claim 1, wherein the valve is biased towards the closed position.

12. The respiratory apparatus of claim 1, further comprising:
a cap configured to engage the proximal end of the instrument introduction section, the cap having an opening that allows for insertion of the instrument into the opening in the proximal end of the instrument introduction section; and
a plug having a plug tether, the plug insertable into the opening in the cap to close the opening in the cap.

13. A respiratory apparatus, comprising:
a manifold configured for connection with an artificial airway of a patient;
an instrument introduction section comprising:
a distal end attached to the manifold for introducing an instrument into the artificial airway of the patient,
a proximal end with an opening, the proximal end configured for releasable attachment to the instrument, the opening in the proximal end allowing for insertion of the instrument into the instrument introduction section, and
a passageway from the opening in the proximal end to an opening in the distal end;
a valve in the instrument introduction section and at least substantially blocking the passageway when in a closed position, the valve having an open position allowing the instrument to be advanced through the instrument introduction section;
a cleaning section provided in the instrument introduction section proximal from the valve;
an irrigation port in communication with the cleaning section, the irrigation port configured for allowing fluid to be transferred therethrough into the cleaning section;
a plug engageable with the proximal end of the instrument introduction section, the plug being adapted for isolating the passageway from the environment through the opening in the proximal end of the instrument introduction section; and
a cap configured to engage the proximal end of the instrument introduction section, the cap having an opening that allows for insertion of the instrument into the opening in the proximal end of the instrument introduction section; and
a tether connecting the plug to the cap, and wherein the plug being insertable into the opening in the cap to close the opening in the cap while at the same time isolating the passageway of the instrument introduction section from the environment through the opening in the proximal end and the opening in the cap.

14. The respiratory apparatus of claim 13, wherein the manifold has at least two proximal ports rotatable so as to be in axial alignment with a distal port of the manifold, no more than one of the proximal ports being in axial alignment with the distal port of the manifold at any one time, and the distal end of the instrument introduction section is attachable to one of the proximal ports of the manifold.

15. The respiratory apparatus of claim 13, wherein the manifold is
an elbow manifold.

16. The respiratory apparatus of claim 13, further comprising a positive end expiratory pressure cap located on the proximal end of the instrument introduction section.

17. The respiratory apparatus of claim 13, wherein the manifold is a T-piece manifold.

18. The respiratory apparatus of claim 13, wherein the manifold is a Y-manifold, and wherein the distal end of the instrument introduction section is attached to a proximal port of the Y-manifold.

19. The respiratory apparatus of claim 13, wherein the instrument is selected from the group consisting of a suction catheter, and endoscope, and a bronchoscope.

20. The respiratory apparatus of claim 13, wherein the instrument is a suction catheter, and wherein the proximal end of the instrument introduction section configured for releasable attachment to the suction catheter.

21. The respiratory apparatus of claim 13, further comprising a wiper seal located in the instrument introduction section proximal from the valve.

22. The respiratory apparatus of claim 13, wherein the valve is a single flap.

23. The respiratory apparatus of claim 22, wherein the single flap has an aperture therethrough, the single flap being configured to be opened by insertion of the instrument through the instrument introduction section.

24. The respiratory apparatus of claim 13, wherein the valve is biased towards the closed position.

25. A respiratory apparatus, comprising:
a manifold attached to the distal end of the instrument introduction section, the manifold in communication with the artificial airway of a patient, the manifold has at least two proximal ports that are rotatable so as to be in axial alignment with a distal port of the manifold, no more than one of the proximal ports being in axial alignment with the distal port of the manifold at any one time, and the distal end of the instrument introduction section attachable to one of the proximal ports of the manifold;
an instrument introduction section comprising:
a distal end attached to one of the proximal ports of the manifold for introducing an instrument into the artificial airway of the patient,
a proximal end with an opening, the proximal end configured for releasable attachment to the instrument, the opening in the proximal end allowing for insertion of the instrument into the instrument introduction section, and
a passageway from the opening in the proximal end to an opening in the distal end;
a single flap valve located in the instrument introduction section and at least substantially blocking the passageway when in a closed position, the single flap valve having an open position allowing the instrument to be advanced through the instrument introduction section;
a cleaning section defined by the instrument introduction section proximal from the single flap valve;
an irrigation port in communication with the cleaning section, the irrigation port configured for allowing fluid to be transferred therethrough into the cleaning section;
a cap configured to engage the proximal end of the instrument introduction section, the cap having an opening that allows for insertion of the instrument into the opening in the proximal end of the instrument introduction section; and
a plug connected to the cap by a tether, the plug insertable into the opening in the cap to close the opening in the cap.

* * * * *